United States Patent
Rowe

(10) Patent No.: US 11,480,053 B2
(45) Date of Patent: Oct. 25, 2022

(54) BIAS CORRECTION FOR A GAS EXTRACTOR AND FLUID SAMPLING SYSTEM

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 227 days.

(21) Appl. No.: 16/674,376

(22) Filed: Nov. 5, 2019

(65) Prior Publication Data

US 2020/0256188 A1  Aug. 13, 2020

Related U.S. Application Data

(60) Provisional application No. 62/804,258, filed on Feb. 12, 2019.

(51) Int. Cl.
*E21B 49/08* (2006.01)
*G01N 1/22* (2006.01)
*E21B 21/06* (2006.01)

(52) U.S. Cl.
CPC .......... *E21B 49/084* (2013.01); *E21B 21/067* (2013.01); *G01N 1/2294* (2013.01); *E21B 49/0875* (2020.05)

(58) Field of Classification Search
CPC .. E21B 49/084; E21B 21/067; E21B 49/0875; G01N 1/2294

(Continued)

(56) References Cited

U.S. PATENT DOCUMENTS 519,509 A   5/1894  Steen
3,118,738 A   1/1964  Jamieson
(Continued)

FOREIGN PATENT DOCUMENTS

EP   0185827 A1   7/1986
EP   2796663 A2   10/2014
(Continued)

OTHER PUBLICATIONS

US 7,246,661 B2, 07/2007, Carlson (withdrawn)
(Continued)

*Primary Examiner* — John Fitzgerald
*Assistant Examiner* — Rodney T Frank
(74) *Attorney, Agent, or Firm* — Delizio, Peacock, Lewin & Guerra

(57) ABSTRACT

A method for analyzing a drilling fluid receiving a drilling fluid sample from a flow of the drilling fluid at a surface of a borehole being drilled in a subterranean formation and extracting, using a gas extraction and sampling system, a dissolved gas from the drilling fluid sample. The method includes determining, using a gas chromatograph, a concentration over time of at least one chemical species of a dissolved gas from the drilling fluid sample and generating an area per concentration curve based on the concentration over time. The method includes determining, using a gas extraction and sampling system, at least one concentration value of the at least one chemical species of the dissolved gas from the drilling fluid sample and correcting bias caused by the gas extraction and sampling system, wherein correcting the bias comprises modifying the at least one concentration value based on the area per concentration curve.

20 Claims, 11 Drawing Sheets

(58) Field of Classification Search
USPC .................................................. 73/152.55
See application file for complete search history.

(56) References Cited

U.S. PATENT DOCUMENTS

| | | | |
|---|---|---|---|
| 3,164,720 A | 1/1965 | Armistead |
| 4,298,572 A | 11/1981 | Moffet et al. |
| 4,492,862 A | 1/1985 | Grynberg et al. |
| 4,524,420 A | 6/1985 | Glodo et al. |
| 4,635,735 A | 1/1987 | Crownover |
| 4,765,182 A | 8/1988 | Boone |
| 4,887,464 A | 12/1989 | Tannenbaum et al. |
| 4,904,603 A | 2/1990 | Jones et al. |
| 5,007,488 A | 4/1991 | Donovan |
| 5,090,256 A | 2/1992 | Issenmann |
| 5,237,539 A | 8/1993 | Selman |
| 5,251,144 A | 10/1993 | Ramamurthi |
| 5,351,532 A | 10/1994 | Hager |
| 5,469,917 A | 11/1995 | Wolcott |
| 5,648,603 A | 7/1997 | Hanson |
| 5,846,056 A | 12/1998 | Dhindsa et al. |
| 6,290,000 B1 | 9/2001 | Zamfes |
| 6,391,094 B2 | 5/2002 | Ramos |
| 6,411,908 B1 | 6/2002 | Talbott |
| 6,661,000 B2 | 12/2003 | Smith et al. |
| 6,666,099 B2 | 12/2003 | Taylor |
| 6,704,689 B1 | 3/2004 | Hogan et al. |
| 6,993,446 B2 | 1/2006 | Gunawardana et al. |
| 6,995,360 B2 | 2/2006 | Jones et al. |
| 7,287,585 B2 | 10/2007 | Carlson |
| 7,328,128 B2 | 2/2008 | Bonanni et al. |
| 7,346,460 B2 | 3/2008 | Difoggio et al. |
| 7,392,138 B2 | 6/2008 | Frechin et al. |
| 7,395,691 B2 | 7/2008 | Sterner et al. |
| 7,465,426 B2 | 12/2008 | Kerherve et al. |
| 7,529,626 B1 | 5/2009 | Ellis |
| 7,637,151 B2 | 12/2009 | Raghuraman et al. |
| 7,650,950 B2 | 1/2010 | Leuchtenberg |
| 7,658,094 B2 | 2/2010 | Brumboiu et al. |
| 7,695,629 B2 | 4/2010 | Salamitou et al. |
| 7,711,486 B2 | 5/2010 | Thigpen et al. |
| 7,752,906 B2 | 7/2010 | Pop et al. |
| 7,779,667 B2 | 8/2010 | Evrard |
| RE42,245 E | 3/2011 | Thomas |
| 7,957,903 B1 | 6/2011 | Selman et al. |
| 7,962,319 B2 | 6/2011 | Grayson |
| 7,979,240 B2 | 7/2011 | Fielder |
| 8,011,238 B2 | 9/2011 | Hanson |
| 8,016,050 B2 | 9/2011 | Teodorescu |
| 8,038,342 B2 | 10/2011 | Dalmazzone et al. |
| 8,056,408 B2 | 11/2011 | Pop et al. |
| 8,132,452 B1 | 3/2012 | Selman et al. |
| 8,204,697 B2 | 6/2012 | Garvey et al. |
| 8,262,909 B2 | 9/2012 | Angelescu et al. |
| 8,265,915 B2 | 9/2012 | Hsu et al. |
| 8,342,004 B2 | 1/2013 | Richards |
| 8,347,957 B2 | 1/2013 | Stephenson et al. |
| 8,374,834 B2 | 2/2013 | Bailey et al. |
| 8,417,495 B2 | 4/2013 | Dashevskiy |
| 8,445,841 B2 | 5/2013 | Szobota et al. |
| 8,499,614 B2 | 8/2013 | Calleri |
| 8,536,524 B2 | 9/2013 | Pomerantz et al. |
| 8,554,717 B2 | 10/2013 | Reckmann et al. |
| 8,556,001 B2 | 10/2013 | Calleri |
| 8,569,685 B2 | 10/2013 | Finlay |
| 8,584,518 B2 | 11/2013 | Phillips |
| 8,645,571 B2 | 2/2014 | Downton et al. |
| 8,656,993 B2 | 2/2014 | Brumboiu |
| 8,677,814 B2 | 3/2014 | Evrard |
| 8,682,588 B2 | 3/2014 | Lapierre et al. |
| 8,684,108 B2 | 4/2014 | Turner et al. |
| 8,704,677 B2 | 4/2014 | Prammer |
| 8,708,052 B2 | 4/2014 | Radi |
| 8,714,246 B2 | 5/2014 | Pop et al. |
| 8,720,287 B2 | 5/2014 | Haney et al. |
| 8,825,414 B2 | 9/2014 | Garvey et al. |
| 8,849,586 B1 | 9/2014 | Garvey |
| 8,863,859 B2 | 10/2014 | Koch et al. |
| 8,884,215 B2 | 11/2014 | Gunn et al. |
| 8,899,348 B2 | 12/2014 | Henderson et al. |
| 8,906,690 B2 | 12/2014 | Pomerantz |
| 8,912,000 B2 | 12/2014 | Daniel et al. |
| 8,939,021 B2 | 1/2015 | Daniel et al. |
| 8,969,021 B2 | 3/2015 | Lin |
| 9,080,406 B2 | 7/2015 | Kelleher et al. |
| 9,194,972 B2 | 11/2015 | Van Der et al. |
| 9,228,433 B2 | 1/2016 | Sawyer et al. |
| 9,238,948 B2 | 1/2016 | Gray |
| 9,405,036 B2 | 8/2016 | Kadayam Viswanathan et al. |
| 9,417,162 B2 | 8/2016 | Haney |
| 9,441,430 B2 | 9/2016 | Selman et al. |
| 9,442,218 B2 | 9/2016 | Selman et al. |
| 9,488,750 B2 | 11/2016 | Bright |
| 9,528,372 B2 | 12/2016 | Selman et al. |
| 9,593,576 B2 | 3/2017 | Rowe |
| 9,599,742 B1 | 3/2017 | Selman et al. |
| 9,612,231 B2 | 4/2017 | Pottorf et al. |
| 9,638,630 B2 | 5/2017 | Eddy et al. |
| 9,638,681 B2 | 5/2017 | Zhdaneev et al. |
| 9,720,124 B2 | 8/2017 | Kadayam Viswanathan et al. |
| 9,810,062 B2 | 11/2017 | Akkurt et al. |
| 9,874,087 B2 | 1/2018 | Jay et al. |
| 9,879,489 B2 | 1/2018 | Shanks et al. |
| 9,890,634 B2 | 2/2018 | Mitchell et al. |
| 2004/0014223 A1 | 1/2004 | Audibert et al. |
| 2006/0093523 A1 | 5/2006 | Norman |
| 2006/0254421 A1 | 11/2006 | Boone |
| 2009/0192731 A1 | 7/2009 | De Jesus et al. |
| 2009/0319307 A1 | 12/2009 | Carlson |
| 2010/0018287 A1 | 1/2010 | Iakimov |
| 2010/0042327 A1 | 2/2010 | Garvey et al. |
| 2010/0299119 A1 | 11/2010 | Erikson et al. |
| 2012/0267525 A1 | 10/2012 | Sasai et al. |
| 2013/0090856 A1 | 4/2013 | Godager |
| 2013/0197809 A1 | 8/2013 | Jones et al. |
| 2013/0269933 A1 | 10/2013 | Pomerantz et al. |
| 2013/0275047 A1 | 10/2013 | Selman et al. |
| 2013/0311096 A1 | 11/2013 | Greer et al. |
| 2013/0317750 A1 | 11/2013 | Hunter |
| 2013/0319104 A1 | 12/2013 | Schexnaider et al. |
| 2014/0116776 A1 | 5/2014 | Marx et al. |
| 2014/0121973 A1 | 5/2014 | Buchanan et al. |
| 2014/0208840 A1 | 7/2014 | Bright |
| 2014/0244173 A1 | 8/2014 | Laughlin et al. |
| 2015/0107349 A1 | 4/2015 | Badri et al. |
| 2015/0136961 A1 | 5/2015 | Eddy et al. |
| 2015/0153314 A1 | 6/2015 | Karoum et al. |
| 2015/0177200 A1 | 6/2015 | Richards |
| 2015/0260703 A1 | 9/2015 | Mitchell |
| 2016/0003793 A1 | 1/2016 | Rowe |
| 2016/0010453 A1 | 1/2016 | Breviere et al. |
| 2016/0041132 A1 | 2/2016 | Romer et al. |
| 2016/0102510 A1 | 4/2016 | Mitchell |
| 2016/0131795 A1 | 5/2016 | Bright |
| 2016/0153955 A1 | 6/2016 | Strapoc et al. |
| 2016/0160641 A1 | 6/2016 | Rowe et al. |
| 2016/0168985 A1 | 6/2016 | Betancourt-Pocaterra et al. |
| 2016/0237998 A1 | 8/2016 | Schexnaider |
| 2016/0258922 A1 | 9/2016 | Formolo et al. |
| 2016/0273355 A1 | 9/2016 | Gosney et al. |
| 2016/0312609 A1 | 10/2016 | Ritzmann et al. |
| 2017/0122101 A1 | 5/2017 | Bright |
| 2017/0138136 A1 | 5/2017 | Ochoa et al. |
| 2017/0167257 A1 | 6/2017 | Rowe |
| 2017/0259192 A1 | 9/2017 | Ochoa |
| 2017/0260855 A1 | 9/2017 | Yang et al. |
| 2017/0268333 A1 | 9/2017 | Pickell et al. |
| 2018/0023356 A1 | 1/2018 | Ochoa |

FOREIGN PATENT DOCUMENTS

| | | |
|---|---|---|
| WO | 2004104639 A1 | 12/2004 |
| WO | 2010042383 A2 | 4/2010 |
| WO | 2010111726 A1 | 10/2010 |

(56) References Cited

FOREIGN PATENT DOCUMENTS

| | | |
|---|---|---|
| WO | 2013162400 A1 | 10/2013 |
| WO | 2016077838 A1 | 5/2016 |
| WO | 2017076490 A1 | 5/2017 |
| WO | 2017131606 A1 | 8/2017 |

OTHER PUBLICATIONS

PCT Application Serial No. PCT/US2019/059866, International Search Report, dated Feb. 26, 2020, 3 pages.
PCT Application Serial No. PCT/US2019/059866, International Written Opinion, dated Feb. 26, 2020, 7 pages.

BIAS CORRECTION FOR A GAS EXTRACTOR AND FLUID SAMPLING SYSTEM

BACKGROUND

The disclosure generally relates to the field of drilling operations, and more particularly to bias correction for a gas extractor and drilling fluid sampling system used for drilling operations.

During the drilling of subterranean wells, a fluid is typically circulated through a fluid circulation system that includes a drilling rig and fluid treatment and storage equipment located substantially at or near the surface of the well. The fluid is pumped by a fluid pump through the interior passage of a drill string, through a drill bit and back to the surface through the annulus between the well bore and the drill string. As the well is drilled, fluids including gasses and liquids from the formation may be released and captured as the fluid is circulated. In some instances, the gasses may be wholly or partially extracted from the fluid for analysis, and the fluids may otherwise be analyzed. The gas and fluid analysis may be used to determine characteristics about the formation.

BRIEF DESCRIPTION OF THE DRAWINGS

Embodiments of the disclosure may be better understood by referencing the accompanying drawings.

DESCRIPTION

The description that follows includes example systems, methods, techniques, and program flows that embody aspects of the disclosure. However, it is understood that this disclosure may be practiced without these specific details. For instance, this disclosure refers to extraction and analyzing of a drilling fluid sample in illustrative examples. Aspects of this disclosure can be also applied to other types of fluids. In other instances, well-known instruction instances, protocols, structures, and techniques have not been shown in detail in order not to obfuscate the description.

Various embodiments include gas analysis of drilling fluid during drilling operations. In particular, various embodiments may provide bias correction for a drilling fluid sampling and gas extraction and analysis system. Such correction can produce composition results from gas analysis that are similar to reservoir composition for methane through pentane. As drilling fluid returns to the surface during drilling, a sample of the drilling fluid can be captured. The drilling fluid returning to the surface may include fluid from the surrounding formation around the borehole. In some embodiments, the sample may be captured in a vessel that minimizes dissolved formational gas loss. The sample can then be recirculated through an extractor continuously to extract dissolved gas. The flowing extracted gas is extracted and placed in a gas chromatograph for analysis. The gas chromatograph can analyze methane through pentane. The concentration of each chemical species may be plotted against time.

For each plot, the area under the curve can be integrated numerically or with a fitted curve against time by concentration to produce an area per concentration curve. Additionally, the area per concentration can be fitted with a response curve. The response curve can then be applied to original data to correct concentrations for system bias. Accordingly, in some embodiments, extraction parameters are not taken into account to create the response curve. Thus, various embodiments do not need to take into account the specific parameters for the extractor and analyzer system to correct values of the concentration species caused by a bias from the system. Examples of the specific parameters not taken into account can include a liquid flow rate through the system, a gas flow rate through the system, processing temperature of the system, etc. Additionally, various embodiments provide for faster processing without sacrificing accuracy for values of the concentration species of the drilling fluid sample. Also, correction is based on sampling at the well site.

Example Drilling System

Figure 1:
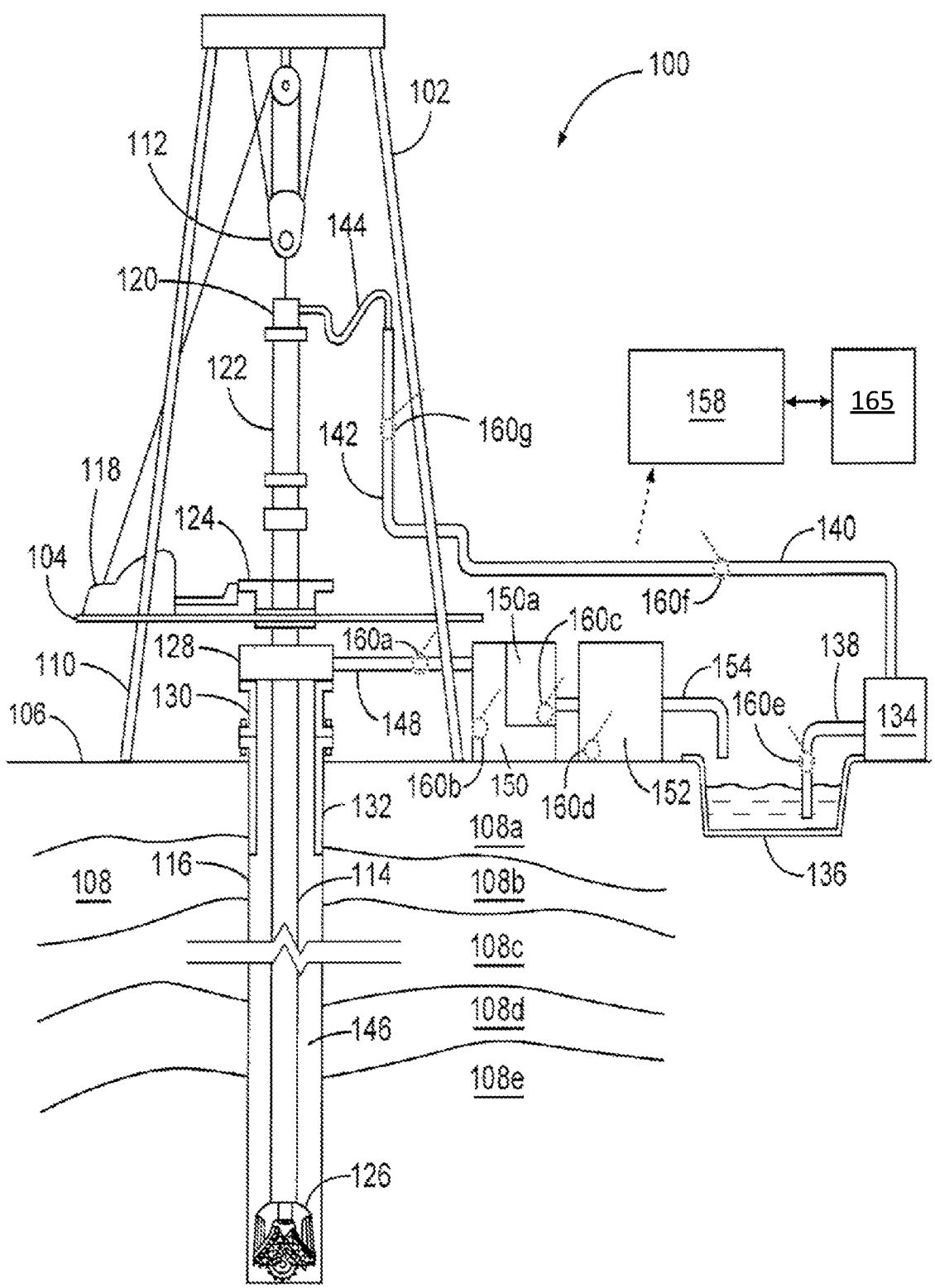
FIG. 1 depicts an example drilling system, according to some embodiments.

FIG. 1 depicts an example drilling system, according to some embodiments. In the embodiment shown, a drilling system 100 includes a derrick 102 mounted on a floor 104 that is in contact with a surface 106 of a formation 108 through supports 110. The formation 108 may be comprised of a plurality of rock strata 108 a-e, each of which may be made of different rock types with different characteristics. At least some of the strata may be porous and contain trapped fluids comprising liquid and gaseous components. Although the drilling system 100 includes an "on-shore" drilling system in which floor 104 is at or near the surface, similar "off-shore" drilling systems are also possible and may be characterized by the floor 104 being separated by the surface 106 by a volume of water.

The derrick 102 may comprise a traveling block 112 for raising or lowering a drill string 114 disposed within a borehole 116 in the formation 108. A motor 118 may control the position of the traveling block 112 and, therefore, the drill string 114. A swivel 120 may be connected between the traveling block 112 and a kelly 122, which supports the drill string 114 as it is lowered through a rotary table 124. A drill bit 126 may be coupled to the drill string 114 and driven by a downhole motor (not shown) and/or rotation of the drill string 114 by the rotary table 124. As bit 126 rotates, it creates the borehole 116, which passes through one or more rock strata or layers of the formation 108.

The drill string 114 may extend downwardly through a bell nipple 128, blowout preventer (BOP) 130, and wellhead 132 into the borehole 116. The wellhead 132 may include a portion that extends into the borehole 116. In certain embodiments, the wellhead 132 may be secured within the borehole 116 using cement. The BOP 130 may be coupled to the wellhead 132 and the bell nipple 128, and may work with the bell nipple 128 to prevent excess pressures from the formation 108 and borehole 116 from being released at the surface 106. For example, the BOP 130 may comprise a ram-type BOP that closes the annulus between the drill string 114 and the borehole 116 in case of a blowout.

During drilling operations, drilling fluid, such as drilling mud, may be pumped into and received from the borehole 116. In certain embodiments, this drilling fluid may be pumped and received by a fluid circulation system that includes components on and below the surface 106. The fluid circulation system includes fluid containment components, flow actuator components, fluid treatment components and fluid flow conduits through which drilling fluid flows. In the embodiment shown, the fluid circulation system may comprise the fluid circulation, processing, and control elements between the bell nipple 128 and the swivel 120, as will be described below. Specifically, the fluid circulation system may include a mud pump 134 that pumps drilling fluid from a reservoir 136 through a suction line 138 into the drill string 114 at the swivel 120 through one or more fluid conduits, including pipe 140, stand-pipe 142, and hose 144. Once introduced at the swivel 120, the drilling fluid then may flow downhole through the drill string 114, exiting at the drill bit 126 and returning up through an annulus 146 between the drill string 114 and the borehole 116 in an open-hole embodiments, or between the drill string 114 and a casing (not shown) in a cased borehole embodiment. While in the borehole 116, the drilling fluid may capture liquids and gasses from the formation 108 as well as particulates or cuttings that are generated by the drill bit 126 engaging with the formation 108.

In certain embodiments, the fluid circulation system further may comprise a return line 148 coupled to the bell nipple 128. Drilling fluid may flow through the return line 148 as it exits the annulus 146 via the bell nipple 128. The fluid circulation system may further comprise one or more fluid treatment mechanisms coupled to the return line 148 that may separate the particulates from the returning drilling fluid before returning the drilling mud to the reservoir 136, where it can be recirculated through the drilling system 100. In the embodiment shown, the fluid treatment mechanisms may comprise a mud tank 150 (which may also be referred to as a header box or possum belly) and a shale shaker 152. The mud tank 150 may receive the flow of drilling fluid from the annulus 146 and slow it so that the drilling fluid does not flow past the shale shaker 152. The mud tank 150 may also allow for cuttings to settle and gasses to be released. In certain embodiments, the mud tank 150 may comprise a trap box 150*a* (sometimes referred to as gumbo trap), which captures heavy clay particulates before the drilling fluid moves to the shale shaker 152, which may separate fine particulates from the drilling fluid using screens. The drilling fluid may flow from the fluid treatment mechanisms into the reservoir 136 through fluid conduit 154.

According to aspects of the present disclosure, the drilling system 100 may further include a fluid analyzer 158 that receives drilling fluid samples from the fluid circulation system. The fluid analyzer 158 analyzes the liquid portions of the drilling fluid and extracts and analyzes gases within the drilling fluid, which can, in turn, be used to characterize the formation 108. The fluid analyzer 158 may comprise a stand-alone machine or mechanism or may comprise integrated functionality of a larger analysis/extraction mechanism. The fluid analyzer 158 may be in fluid communication with and receive drilling fluid samples from access points within the fluid circulation system, including, but not limited to, access point 160*a* on the return line 148, access point 160*b* on the mud tank 150, access point 160*c* on the trap box 150*a*, access point 160*d* on the shale shaker 152, access point 160*e* on the suction line 138, access point 160*f* on the pipe 140, and access point 160*g* on the stand pipe 142. Fluid communication may be provided via at least one probe in fluid communication with the flow of drilling fluid at any one of the access points. In other embodiments, the drilling fluid analyzer 158 may be coupled to one or more of the fluid channels such that the flow of drilling fluid passes through the fluid analyzer 158.

At least some of the strata 108*a-e* may contain trapped liquids and gasses that are held under pressure. As the borehole 116 penetrates new strata, some of these fluids may be released into the borehole 116. The released fluids may become suspended or dissolved in the drilling fluid as it exits the drill bit 126 and travels through the borehole annulus 146. Each released liquid and gas may be characterized by its chemical composition, and certain formation strata may be identified by the liquids and gasses it contains. As will be described below, the fluid analyzer 158 may take periodic or continuous samples of the drilling fluid, for example, by pumping, gravity drain or diversion of flow, or other means. The fluid analyzer 158 may generate corresponding measurements of the fluid sample or extracted gas from the fluid sample that may be used to determine the chemical composition of the drilling fluid. This chemical composition may be used to determine the types of liquids and gasses that are suspended within the drilling fluid, which can then be used to determine a formation characteristic of the formation 108.

The fluid analyzer 158 may include or be communicably coupled to a device 165. In the embodiment shown, the device 165 comprises a computing system located at the surface that may receive measurements from the fluid analyzer 158 and process the measurements to determine at least one formation characteristic based on the drilling fluid sample. For example, the device 165 may include a processor configured to execute program code stored on a machine-readable medium.

In certain embodiments, the device 165 may further control the operation of the drilling fluid analyzer 158, including how often the drilling fluid analyzer 158 takes measurements and fluid samples. In certain embodiments, the device 165 may integrated with the fluid analyzer 158. In other embodiments, the device 165 may be a distinct system configured to receive measurements from a variety of devices in the drilling system 100 and/or control the operation of other devices.

The output of the fluid analyzer 158 may comprise electrical signals and/or electronically encoded data that corresponds to measurements taken by the fluid analyzer 158 of liquids and/or extracted gases from the drilling fluid samples. In certain embodiments, the device 165 may receive the output from the fluid analyzer 158 and determine characteristics of the liquid and/or extracted gas from the drilling fluid sample, such as corresponding chemical compositions of liquid and/or gaseous components. The chemical compositions of the drilling fluid may comprise the types of chemicals found in the drilling fluid sample and their relative concentrations. The device 165 may determine the chemical composition, for example, by receiving an output from fluid analyzer 158, and comparing the output to a first data set corresponding to known chemical compositions. In certain embodiments, the device 165 may fully characterize the chemical composition of the drilling fluid sample based on the output from the fluid analyzer 158. The device 165 may further determine the types of liquids and gasses suspended within the drilling fluid based on the determined chemical composition. Additionally, in certain embodiments, the device 165 may determine a characteristic of the formation 108 using the determined types and concentrations of liquids and gasses suspended within the drilling fluid. The device 165 may be configured to determine formation characteristics by comparing the determined types and concentrations of liquids and gasses suspended within the drilling fluid to a second data set that includes types and concentrations of liquids and gasses suspended within the drilling fluid of known subterranean formations.

The device 165 may determine a formation characteristic using the determined chemical composition. An example determined chemical composition for the liquid portion of a drilling fluid may be 15% chemical/compound A, 20% chemical/compound B, 60% chemical/compound C, and 5% other chemicals/compounds. Example downhole characteristics include, but are not limited to, the type of rock in the formation 108, the presences of hydrocarbons in the formation 108, the production potential for one of more of strata 108a-e, and the movement of fluid within one or more of strata 108a-e. In certain embodiments, the device 165 may determine the formation characteristic using the determined chemical composition characteristics by comparing the determined chemical composition to a second data set that includes chemical compositions of known subterranean formations. For example, the determined chemical composition may correspond to a drilling fluid with suspended fluid from a shale layer in the formation 108.

Figure 2:
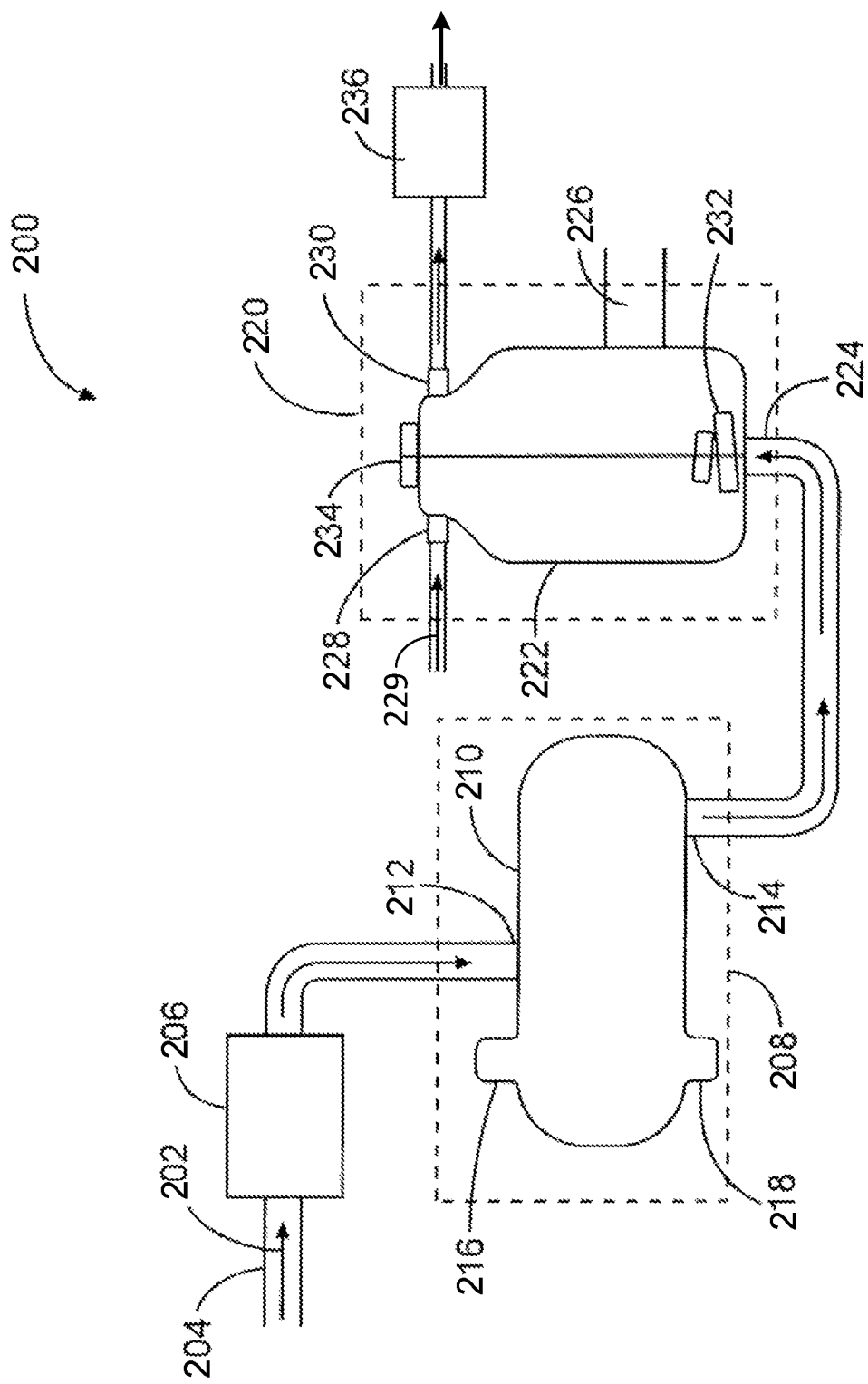
FIG. 2 is a block diagram depicting an example gas extractor system configured to extract gasses from drilling fluid samples, according to some embodiments.

FIG. 2 is a diagram of an example gas extraction system 200 that extracts gasses from a drilling fluid sample, according to some embodiments. The gas extraction system 200 may be included with a drilling system such as the drilling system 100, and may be in selective fluid communication with a flow of drilling fluid through the drilling system, such as at access points similar to those described with reference to FIG. 1. For instance, one or more of the components of gas extraction system 200 may be implemented by fluid analyzer 158. In the embodiment shown, the gas extraction system 200 may receive a drilling fluid sample 202 through a fluid conduit or pipe 204 that is in selective fluid communication with the flow of drilling fluid. As described above, drilling fluid samples may be taken periodically or continuously from the flow of drilling fluid through a fluid circulation system during drilling operation, and the drilling fluid sample 202 may comprise one of those continuous or periodic samples. The gas extraction system 200 may comprise a pump 206 that pushes the drilling fluid sample toward a sample-temperature controller 208 of the gas extraction system 200. The sample-temperature controller 208 may be configured to alter or maintain the temperature of the drilling fluid sample 202 at a set temperature, which may be hotter, cooler, or the same as the temperature of the sample 202 as it enters the gas extraction system 200. In the embodiment shown, the sample-temperature controller 208 comprises a shell and tube heat exchanger with two sets of fluid inlets and outlets: a first inlet 212 and first outlet 214, and a second inlet 216 and second outlet 218. Each set of fluid inlets and outlets may correspond to a different, segregated fluid pathway through the shell 210. For example, the second inlet 216 and second outlet 218 may correspond to a fluid pathway comprising a system of sealed tubes (not shown) located within the shell 210, and the first inlet 212 and first outlet 214 may correspond to a fluid pathway in which fluid flows around the system of sealed tubes. The system of sealed tubes may comprise u-tubes, single-pass straight tubes, double-pass straight tubes, or other configurations.

In certain embodiments, the sample 202 may enter the shell 210 through first inlet 212 and exit through first outlet 214. A second fluid or gas may enter the shell 210 through second inlet 216 and exit through second outlet 218. Either the second fluid or the drilling fluid sample 202 may flow through the system of sealed tubes. The second fluid may be at or near a desired set temperature for the drilling fluid sample 202, and energy transfer may occur between the sample 202 and the second fluid through the tubes, which may conduct thermal energy, until the sample 202 has reached the desired set temperature. Notably, although a shell and tube heat exchanger are described herein, the sample-temperature controller 208 may comprise other types of heat exchangers, including, but not limited to, thermoelectric, electric, and finned tube heat exchanger that are driven by electricity, gas, or liquid; u-tube heat exchangers; etc.

Once at or near the set temperature, the drilling fluid sample 202 may be received at a gas extractor 220 of the gas extraction system 200, the gas extractor 220 being in fluid communication with the sample-temperature controller 208. Example gas extractors include, but are not limited to, continuously stirred vessels, distillation columns, flash columns, separator columns, or any other vessel that allows for the separation and expansion of gas from liquids and solids. In the embodiment shown, the gas extractor 220 comprises a vessel 222 that receives the sample 202 through a fluid inlet 224 and further comprises a fluid outlet 226 through which a portion of the sample 202 will flow after a gas extraction process. The gas extractor 220 may further comprise an impeller 232 within the vessel 222 to agitate the sample 202 as it enters the vessel 222. The impeller 232 may be driven by a motor 234 that rotates the impeller to create a turbulent flow of the sample 202 within the vessel, which causes gasses trapped within the solids and liquids of the sample 202 to be released into the vessel 222. Although an impeller 232 is shown it is possible to use other types of agitators.

Gasses within the vessel 222 that are released from the sample 202 through the agitation process may be removed from the vessel through a gas outlet 230. In certain embodiments, the vessel 222 may comprise a gas inlet 228, and at least one carrier gas 229 may be introduced into the vessel 222 through the gas inlet 228. Carrier gasses 229 may comprise atmospheric or purified gasses that are introduced into the vessel 222 to aide in the movement of the extracted gasses to a gas outlet 230. The carrier gasses may have known chemical compositions such that their presence can be accounted for when the extracted gasses from gas outlet 230 are analyzed.

Although the sample-temperature controller 208 and gas extractor 220 are shown as separate devices, it may be possible to combine the functionality into a single device. For example, heat exchange may be accomplished through the vessel 222, bringing the sample 202 to a set temperature while it is in the vessel 222. In other embodiments, the sample-temperature controller 208 may be optional, and the sample 202 may be directed to the extractor 220 without flowing through a sample-temperature controller 208. In certain embodiments, the gas outlet 230 of the extractor 220 may be coupled to a pump 236 which may deliver the extracted gas sample out from the extractor 220.

Figure 3:
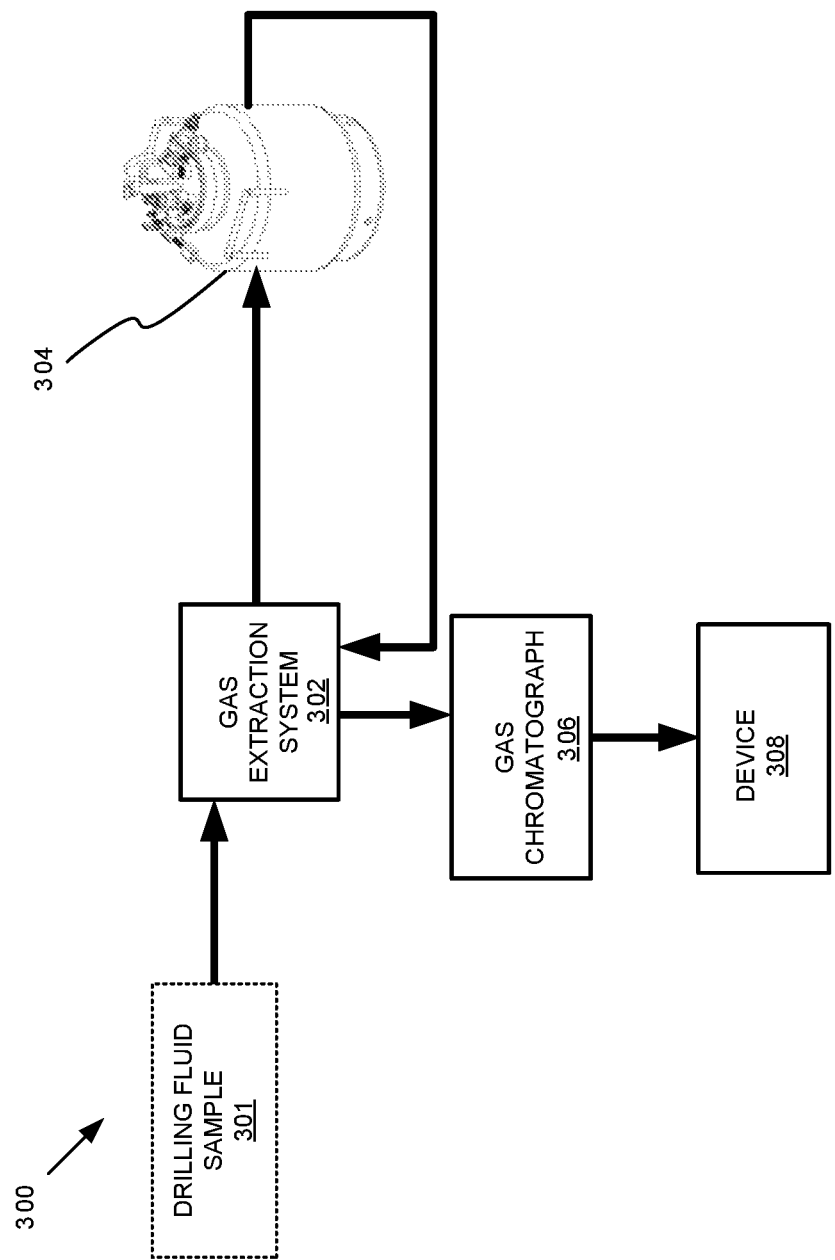
FIG. 3 is a block diagram depicting an example system for drilling fluid sampling and gas extraction and analysis, according to some embodiments.

FIG. 3 depicts an example system 300 for drilling fluid sampling and gas extraction and analysis, according to some embodiments. The system 300 includes a gas extraction system 302, a vessel 304, a gas chromatograph 306, and a device 308. An example of the gas extraction system 302 is the gas extraction system 200 illustrated in FIG. 2. A drilling fluid sample 301 is input into the gas extraction system 302. Once the measured concentration of at least one type of species reaches a threshold, the gas extraction system 302 inputs the drilling fluid sample 301 into the vessel 304. For example, once a measured concentration species reaches 100 parts per million (PPM) for the drilling fluid sample, the gas extraction system 302 can input the drilling fluid sample into the vessel 304. Also, an output of the gas extraction system 302 such as the gas output from gas outlet 230 in FIG. 2 is coupled to an input of the gas chromatograph 306 that is configured to measure or otherwise determine concentrations of species based on the extracted gas received from gas extraction system 302. Storage of the sample in the vessel 304 can minimize dissolved formational gas loss.

Additionally, an output of the vessel 304 is coupled back to an input of the gas extraction system 302. The drilling fluid sample can then be recirculated through the gas extraction system 302 continuously to extract dissolved gas while flowing extracted gas extracted in a gas extractor within gas extraction system 302 (e.g., gas extractor 220) to the gas chromatograph 306 for concentration measurement and other analysis. The gas chromatograph 306 may be configured to determine concentration of each species of the extracted gas over time.

In some embodiments, the gas chromatograph 306 is configured to determine species of the drilling fluid sample that includes methane, ethane, propane, isobutane, butane, isopentane, and pentane. The device 308 is coupled to receive values of the concentration of each species of the extracted gas over time from the gas chromatograph 306. The device 308 can by any combination of hardware, software, firmware, etc. configured to perform the operations described herein. For example, the device 308 may include a processor configured to execute program code stored on a machine-readable medium also included in the device 308. As further described below, the device 308 may be configured to plot concentrations of each species versus time. The device 308 may also be configured to generate an area per concentration curve for each chemical species. The device 308 can fit the area per concentration curve with a response curve for each chemical species. The device 308 may also apply the response curve to original values of concentration of each chemical species to create corrected values of concentration of each chemical species to correct for system bias.

Example Operations

Figure 4:
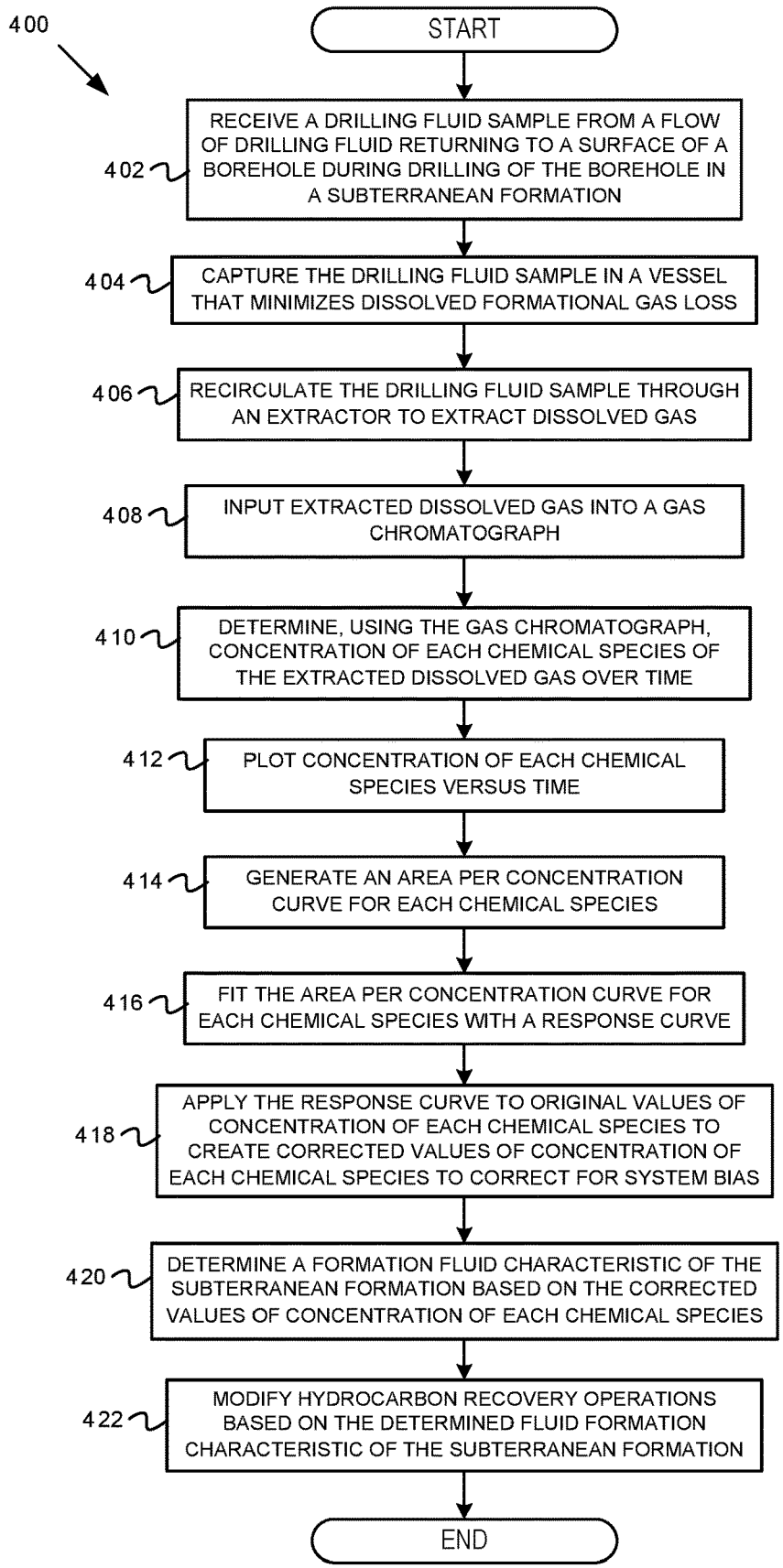
FIG. 4 is a flowchart depicting operations and functions for drilling fluid sampling and gas extraction and analysis, according to some embodiments.

FIG. 4 is a flowchart 400 depicting operations for drilling fluid sampling and gas extraction and analysis, according to some embodiments. Operations of flowcharts 400 may be performed by software, firmware, hardware or a combination thereof. The operations of the flowchart 400 start at block 402.

At block 402, a drilling fluid sample is received from a flow of drilling fluid returning to a surface of a borehole during drilling of the borehole in a subterranean formation. For example, the drilling fluid sample may be received from one or more access points within a drilling fluid circulation system such as depicted and described with reference to FIG. 1.

At block 404, the drilling fluid sample is captured in a vessel that minimizes dissolved formational gas loss. For example with reference to FIG. 3, the extraction system 302 outputs the drilling fluid sample for storage in the vessel 304 that is pressure sealed to minimize loss of formation gas.

At block 406, the drilling fluid sample is circulated and recirculated through the gas extractor to extract dissolved gas. For example with reference to FIG. 3, the gas extraction system 302 receives the drilling fluid sample back from the vessel 304 to be recirculated through the gas extraction system 302 to extract dissolved gas from the drilling fluid sample.

At block 408, extracted dissolved gas is input into a gas chromatograph. For example with reference to FIG. 3, the gas extraction system 302 inputs the extracted dissolved gas into the gas chromatograph 306.

At block 410, a concentration of each chemical species of the extracted dissolved gas over time is determined using the gas chromatograph. For example with reference to FIG. 3, the gas chromatograph 306 determines concentration of each chemical species of the extracted dissolved gas over time received from the gas extraction system 302.

Figure 5:
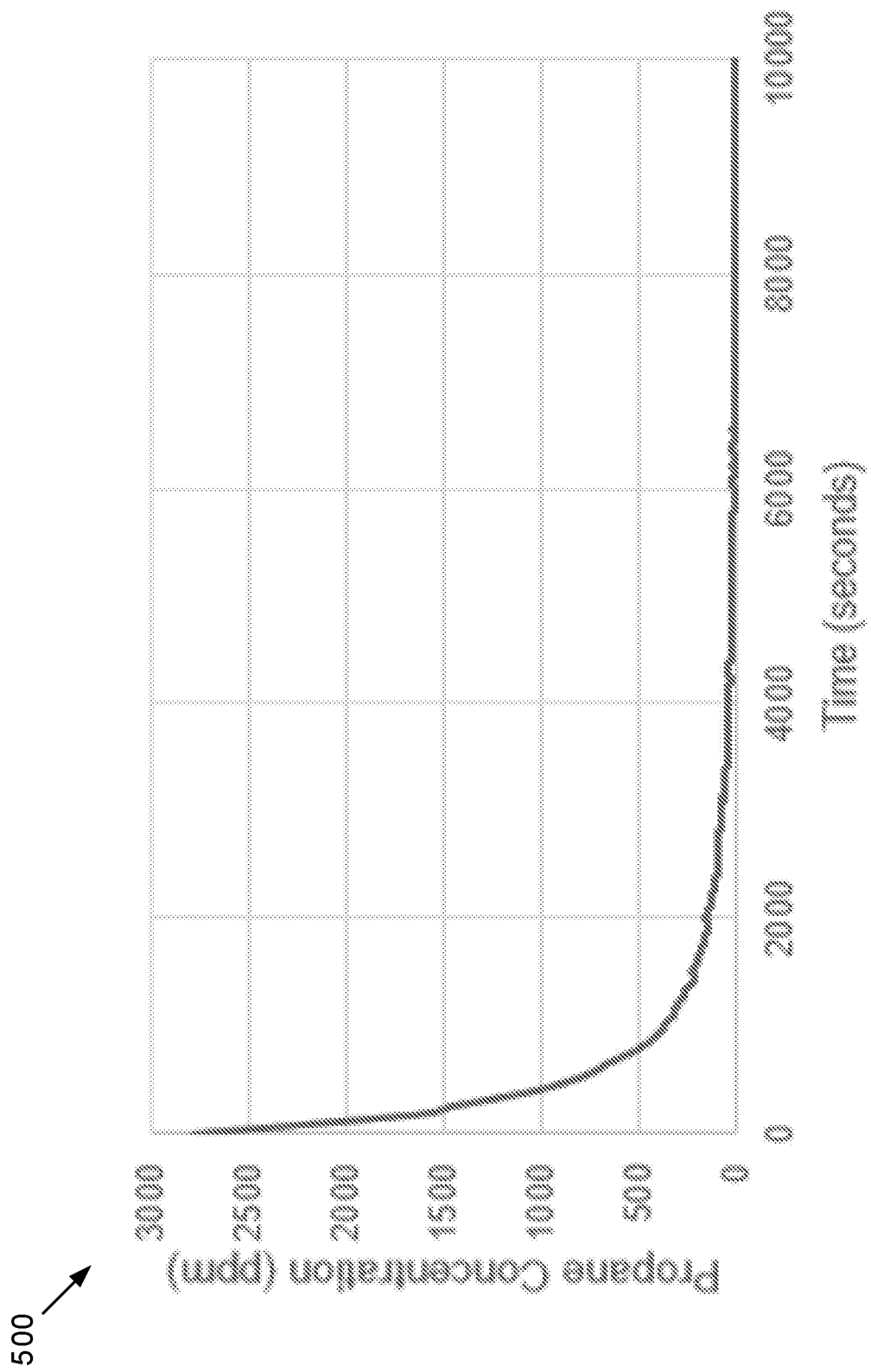
FIG. 5 is a graph depicting an example concentration over time, according to some embodiments.

At block 412, a concentration of each chemical species is plotted versus time. For example with reference to FIG. 3, the device 308 may receive the concentration of each chemical species from the gas chromatograph 306 and plot a concentration of each chemical species versus time. To illustrate, FIG. 5 depicts a graph of an example concentration over time, according to some embodiments. In particular, FIG. 5 depicts a graph 500 of propane concentration in parts per million (PPM) along the Y-axis and time in seconds along the X-axis.

Figure 6:
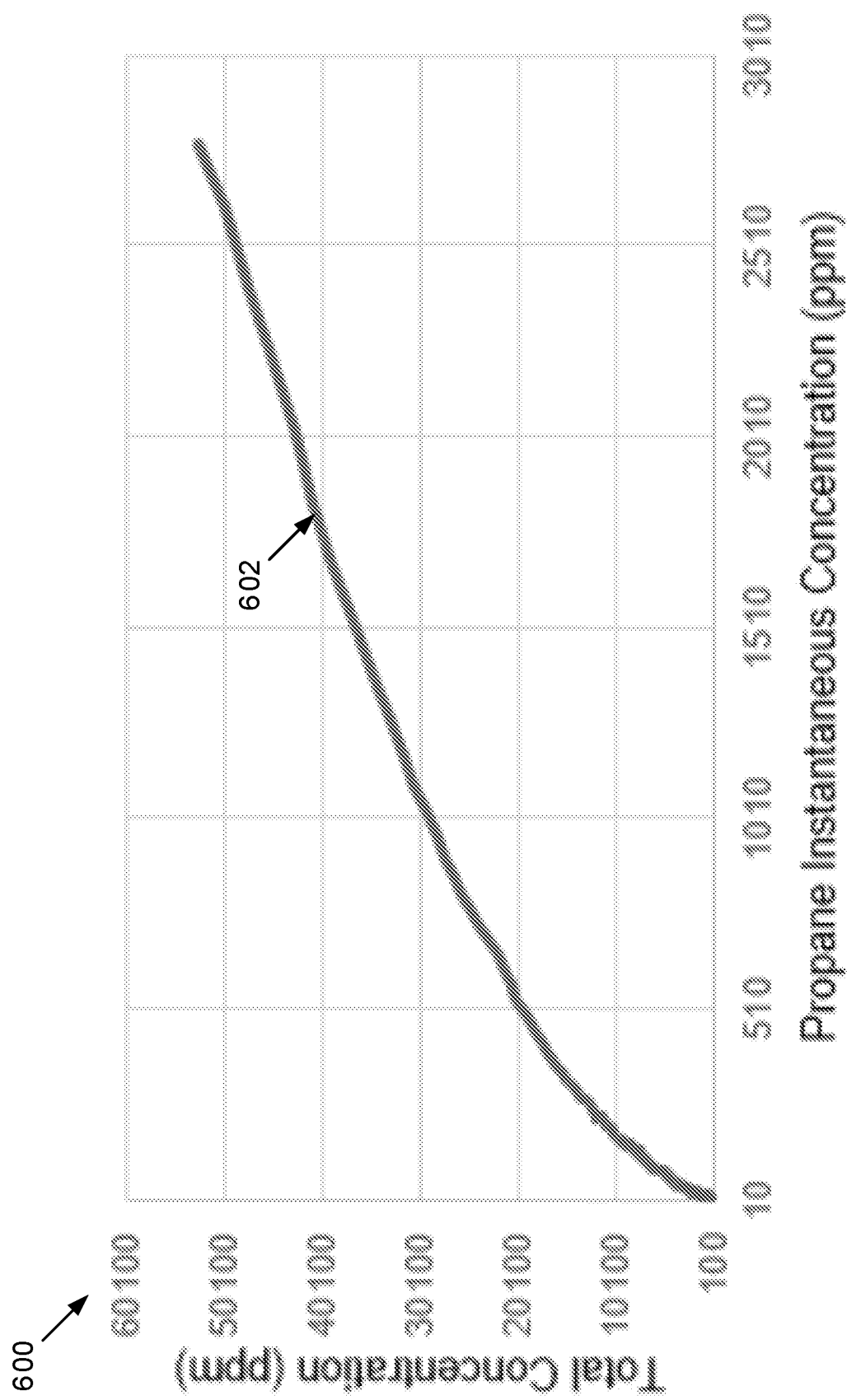
FIG. 6 is a graph depicting an area per concentration curve derived from the example concentration over time of FIG. 5, according to some embodiments.

At block 414, an area per concentration curve is generated for each chemical species. For example with reference to FIG. 3, the device 308 can generate an area per concentration curve for each chemical species based on the concentration over time curves generated for each species such as the curve depicted in FIG. 5. In some embodiments, an area per concentration curve is generated by integrating the area under a concentration over time curve at each of a series of points in time. In this manner, the integration generates the area under the curve by generating an area under each time point. An area per concentration curve it generated by depicting the per time point area value as a total concentration value along one axis that varies in accordance with the instantaneous concentration values that are directly measured for each time point. To illustrate, FIG. 6 depicts a graph of an area per concentration curve derived from the example concentration over time of FIG. 5, according to some embodiments. FIG. 6 depicts a graph 600 of total concentration of propane in PPM along the Y-axis and propane instantaneous concentration in PPM along the X-axis. The result is the area under a curve 602. In some embodiments, the device 160 is configured to generate the area under the curve 602 by numerically integrating or using a fitted curve against time by concentration.

Figure 7:
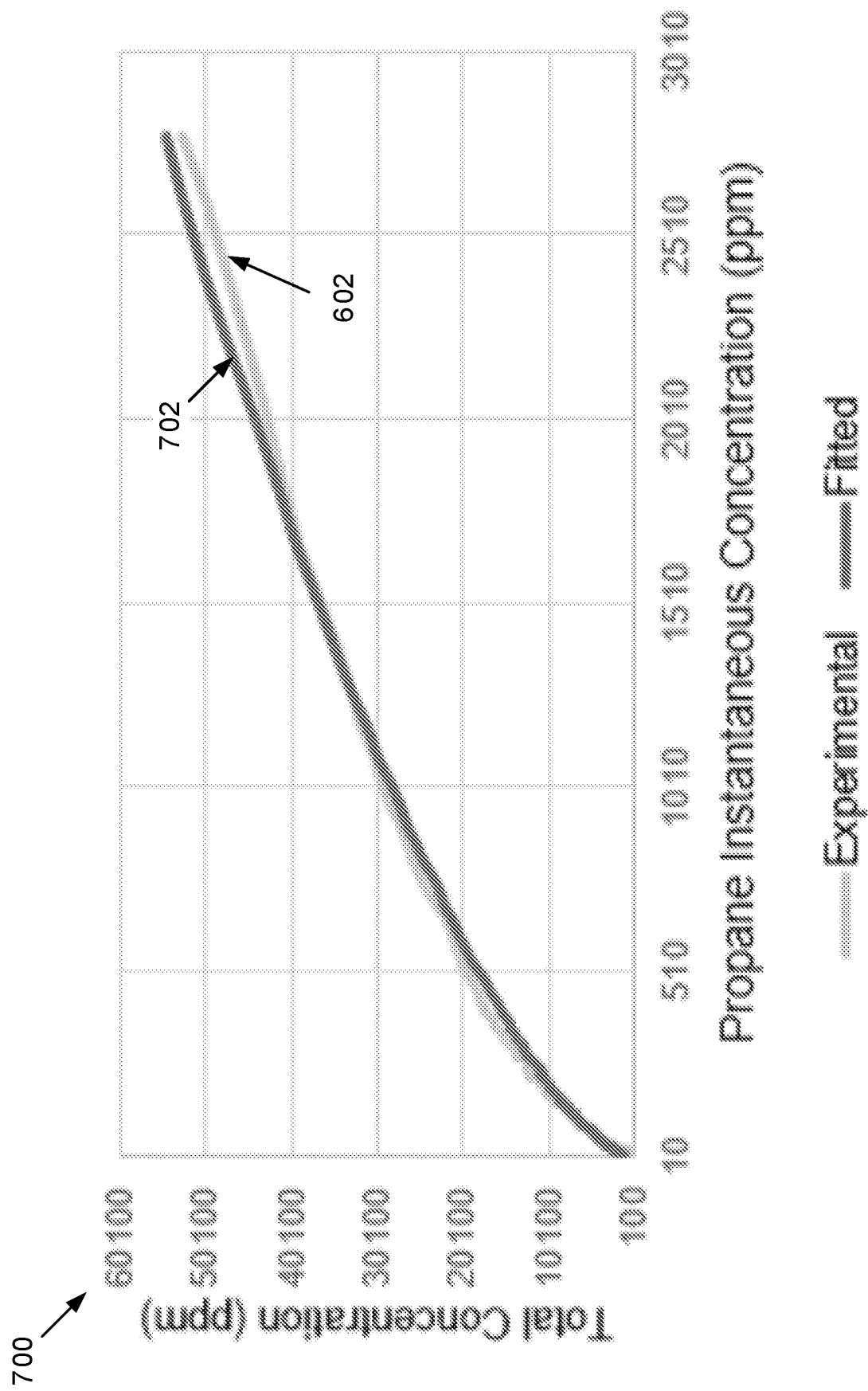
FIG. 7 is a graph depicting the area per concentration curve of FIG. 6 fitted with a response curve, according to some embodiments.

At block 416, the area per concentration curve for each chemical species is fitted with a response curve. For example with reference to FIG. 3, the device 308 can fit the area per concentration curve with a response curve for each chemical species. To illustrate, FIG. 7 depicts a graph 700 of the area per concentration curve 602 of FIG. 6 fitted with a response curve 702, according to some embodiments. The graph 700 presents total concentration of propane in PPM along the Y-axis and propane instantaneous concentration in PPM along the X-axis. The curve 602 derived from the drilling fluid sample from the graph 600 is reproduced on the graph 700. The graph 700 also includes a fitted response curve 702. A best fitted curve is selected. For example, the fitted curved can be power log, polynomial, logarithmic, exponential, etc.

Figure 8:
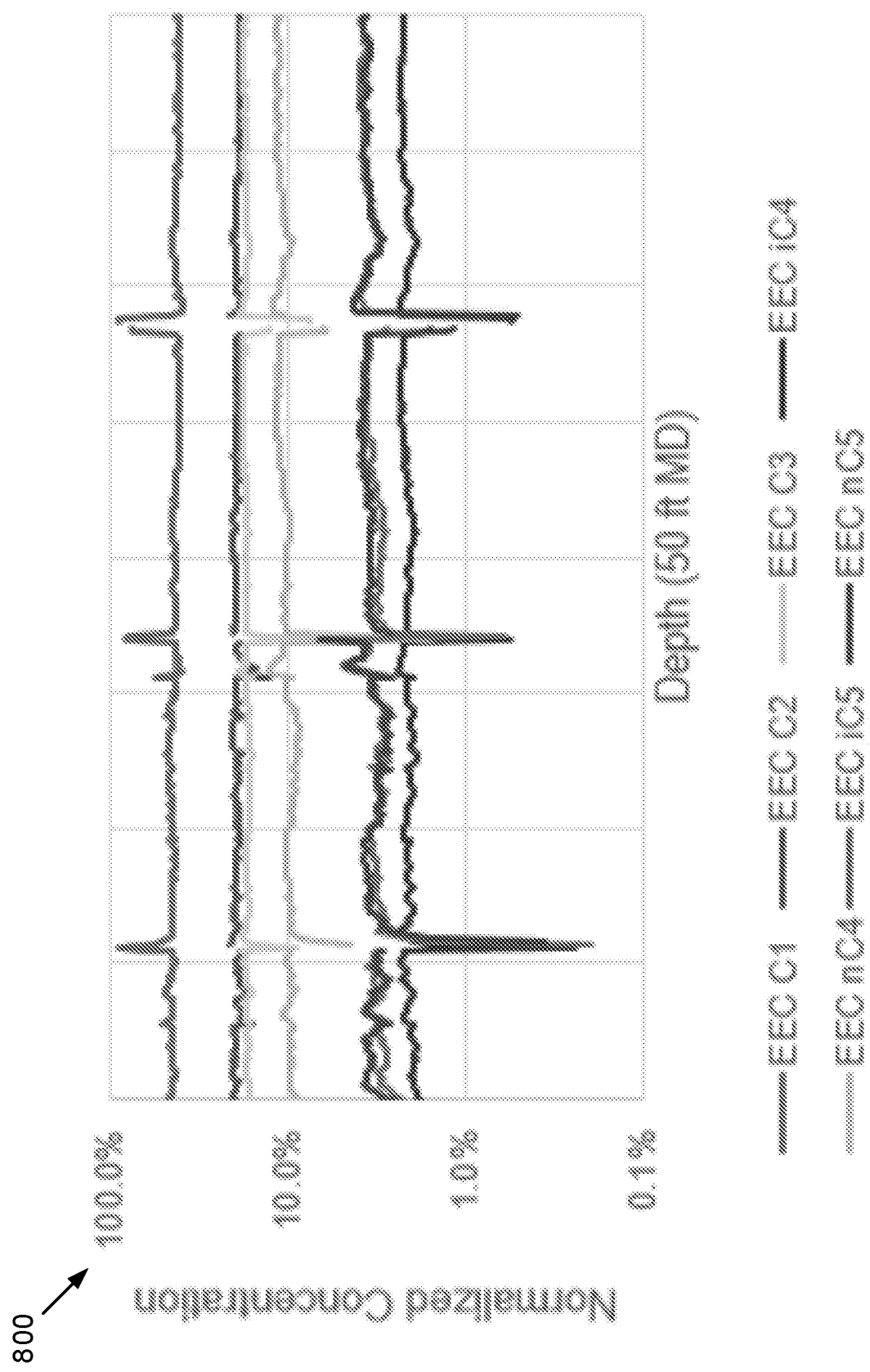
FIG. 8 is a graph depicting an example normalized correction of concentrations using the area under the response curve of FIG. 7, according to some embodiments.
Figure 9:
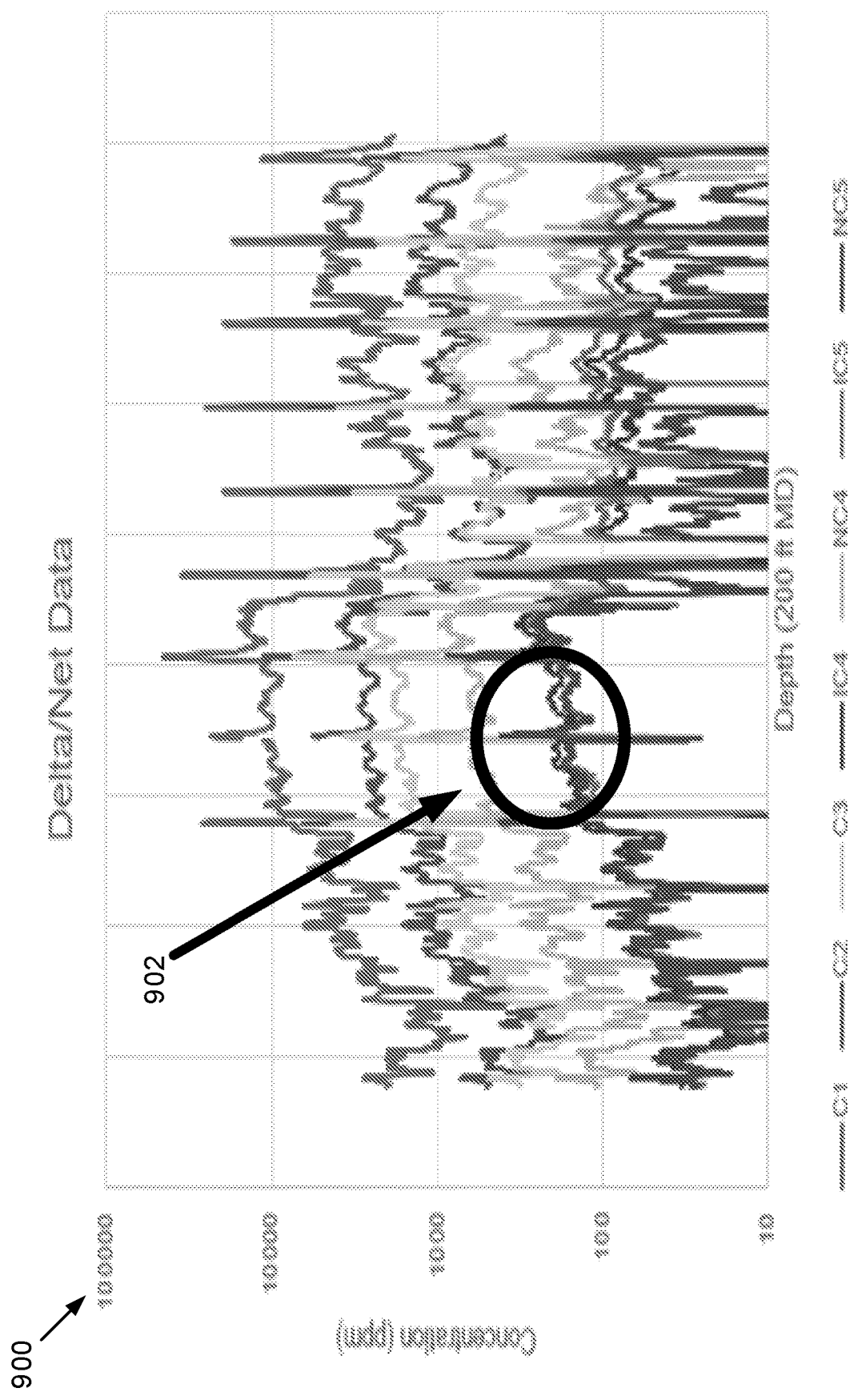
FIG. 9 is a graph depicting example concentrations over a depth of the borehole without correction of system bias, according to some embodiments.
Figure 10:
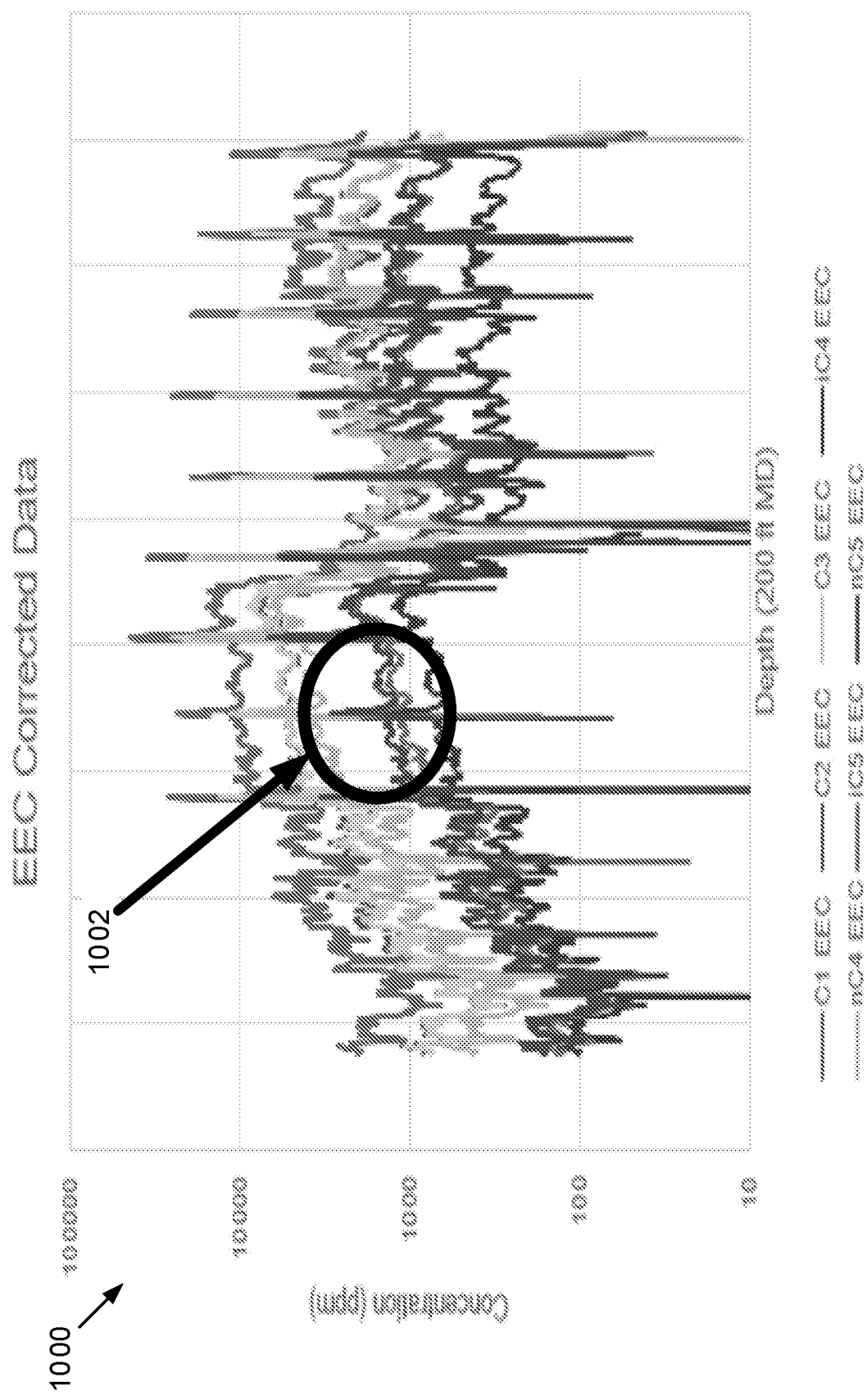
FIG. 10 is a graph depicting the example concentrations over a depth of the borehole of FIG. 9 with correction of system bias, according to some embodiments.

At block 418, the response curve is applied to original values of concentration of each chemical species to create corrected values of concentration of each chemical species to correct for system bias. For example with reference to FIG. 3, the device 308 may be configured to apply the response curve to original values of concentration of each chemical species to create corrected values of concentration of each chemical species to correct for system bias. For example, the fitted curve can be represented as an equation in which a new value is defined as a function of a previously determined value. So each point in time of the raw data is adjusted based on the equation defined by the fitted curve. To illustrate, FIG. 8 depicts a graph of an example normalized correction of concentrations using the area under the response curve of FIG. 7, according to some embodiments. To further illustrate, FIG. 9 depicts a graph of example concentrations over a depth of the borehole without correction of system bias, according to some embodiments. In particular, FIG. 9 depicts a graph 900 of values of seven concentrations (C1, C2, C3, IC4, NC4, IC5, and NC5) in PPM over a range of depth. These values are prior to correction of system bias. For example, an area 902 of the graph 900 highlights the values of the concentration NC5 just greater than 100 PPM. FIG. 10 depicts a graph of the example concentrations over a depth of the borehole of FIG. 9 with correction of system bias, according to some embodiments. FIG. 10 depicts a graph 1000 of values of the seven concentrations of FIG. 9 after correction for system bias. An area 1002 of the graph 1000 corresponds to the area 902 of the graph 900. As shown, the values of the concentration NC5 greater than 1000 PPM because of the adjustment for system bias.

At block 420, a formation characteristic of the subterranean formation is determined based on the corrected values of concentration of each chemical species. For example with reference to FIG. 3, the device 308 can determine a formation characteristic based on the corrected values of concentration of each chemical species. Determining the formation characteristic using the determined chemical composition may comprise comparing the determined chemical composition to known chemical compositions of subterranean formations. The formation characteristics may comprise at least one of a type of rock in the subterranean formation, the presence of hydrocarbons in the subterranean formation, the production potential for a stratum of the subterranean formation, and the movement of fluid within the strata.

At block 422, hydrocarbon recovery operations are modified based on the determined fluid formation characteristic of the subterranean formation. For example, the current drilling operation could be modified (e.g., direction, rate, etc.). Additionally, production operations can be modified. For example, if the determined fluid formation characteristic of the subterranean formation is essentially gas, the production operation is configured for gas production. Conversely, the determined fluid formation characteristic of the subterranean formation is essentially oil, the production operation is configured for oil production. If the determined fluid formation characteristic of the subterranean formation is a combination of oil and gas, the production operation is configured for split production to produce by oil and gas.

Thus, in contrast to conventional approaches, various embodiments do not take into account parameters of the extractor in order to correct for bias of the gas extraction and sampling system. Such embodiments provide for a simpler and easier correction of the bias because the correction is independent the specifics of each system.

Example Computer

Figure 11:
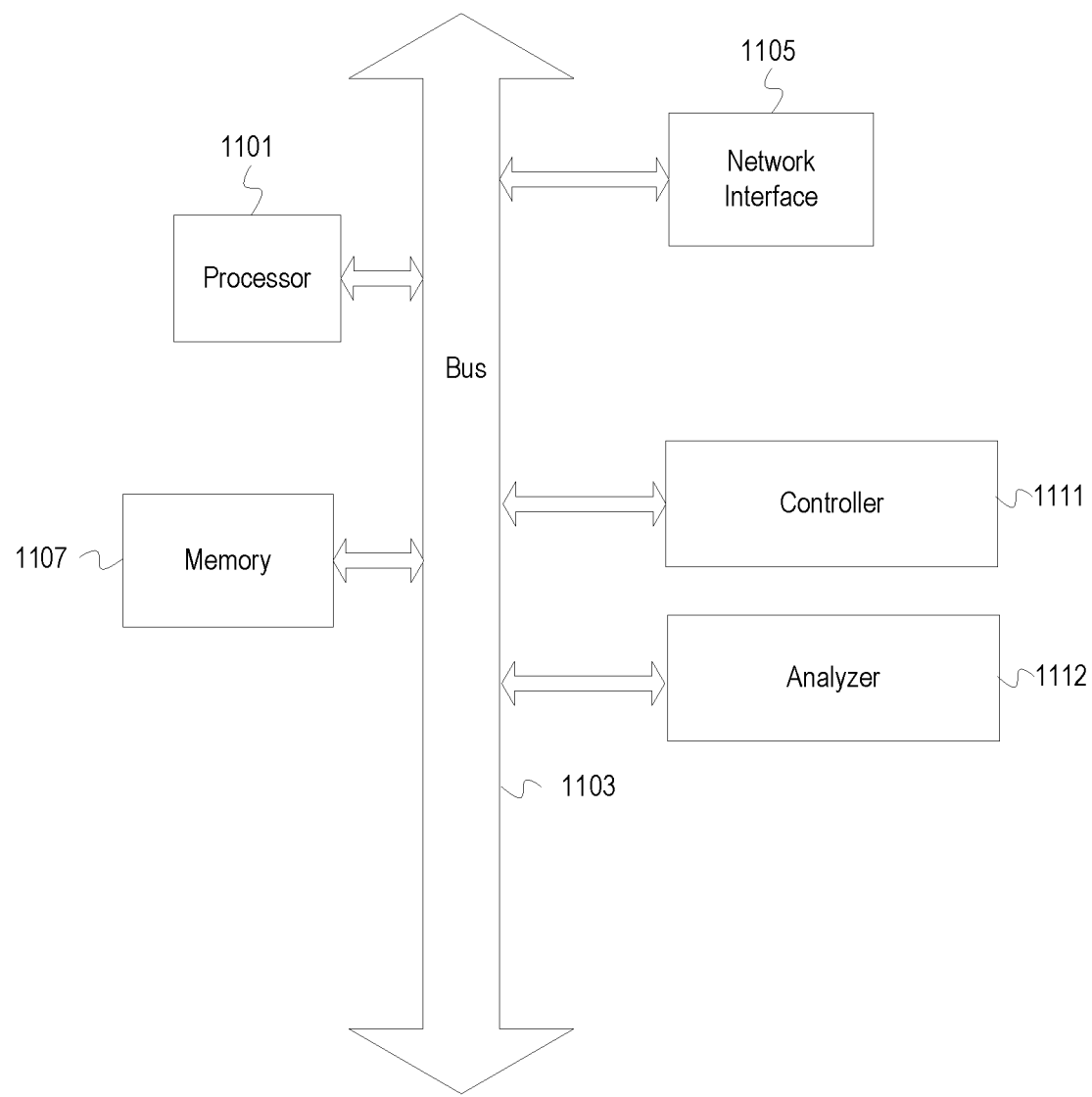
FIG. 11 is a block diagram depicting an example computer, according to some embodiments.

FIG. 11 depicts an example computer, according to some embodiments. The computer includes a processor 1101 (possibly including multiple processors, multiple cores, multiple nodes, and/or implementing multi-threading, etc.). The computer includes memory 1107. The memory 1107 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 1103 (e.g., PCI, ISA, PCI-Express, HyperTransport® bus, InfiniBand® bus, NuBus, etc.) and a network interface 1105 (e.g., a Fiber Channel interface, an Ethernet interface, an internet small computer system interface, SONET interface, wireless interface, etc.).

The computer also includes an analyzer 1112 and a controller 1111 The analyzer 1112 can perform processing and analyzing of a drilling fluid sample (as described above). The controller 1111 can control the different operations that can occur in the response to results from the analysis. For example, the controller 1111 can communicate instructions to the appropriate equipment, devices, etc. to alter different hydrocarbon recovery operations. Any one of the previously described functionalities may be partially (or entirely) implemented in hardware and/or on the processor 1101. For example, the functionality may be implemented with an application specific integrated circuit, in logic implemented in the processor 1101, in a co-processor on a peripheral device or card, etc. Further, realizations may include fewer or additional components not illustrated in FIG. 11 (e.g., video cards, audio cards, additional network interfaces, peripheral devices, etc.). The processor 1101 and the network interface 1105 are coupled to the bus 1103. Although illustrated as being coupled to the bus 1103, the memory 1107 may be coupled to the processor 1101.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain, or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing. Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

Using the apparatus, systems, and methods disclosed herein may provide the ability to monitor changes in down hole particles (e.g., cuttings), so that the impact of drilling fluid properties and activities in the field can be assessed immediately. This ability may be used to increase efficiency by redirecting pumping and drilling operations in real-time, perhaps as part of a closed-loop control system. While the aspects of the disclosure are described with reference to various implementations and exploitations, it will be understood that these aspects are illustrative and that the scope of the claims is not limited to them. In general, techniques for processing and analyzing of particles from downhole as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

EXAMPLE EMBODIMENTS

Embodiment 1: A method comprising: extracting, using a gas extraction and sampling system, a dissolved gas from a drilling fluid sample; determining, using a gas chromatograph, a concentration over time of at least one chemical species of the dissolved gas; generating an area per concentration curve based on the concentration over time of the at least one chemical species; determining at least one concentration value of the at least one chemical species of the dissolved gas from the drilling fluid sample; and modifying the at least one concentration value based on the area per concentration curve. For Embodiment 1, said modifying the at least one concentration value may comprise: fitting the area per concentration curve with a response curve; and applying the response curve to the determined concentration. For Embodiment 1, said modifying the at least one concentration value may further comprise generating a corrected concentration of each species based on said applying the response curve to the determined concentration. For Embodiment 1, the extraction and sampling system may include a heat exchanger and a gas extractor configured to receive the drilling fluid sample from the heat exchanger, and wherein said extracting comprises circulating the drilling fluid sample through the heat exchanger and extracting gasses from the drilling fluid sample within the gas extractor. For Embodiment 1, the method may further comprise during said extracting of the dissolved gas, circulating the drilling fluid sample between the extraction and sampling system and a containment vessel in response to a concentration of a species within the drilling fluid sample reaching a threshold. For Embodiment 1, the method may further comprise receiving a drilling fluid sample from a flow of the drilling fluid at a surface of a borehole within a subterranean formation, wherein said receiving a drilling fluid sample comprises transporting the drilling fluid sample from downhole to the surface of the borehole during drilling operations. For Embodiment 1, the method may further comprise: determining a fluid formation characteristic of the subterranean formation using the at least one modified concentration value; and modifying a hydrocarbon recovery operation based on the determined fluid formation characteristic.

Embodiment 2: A system comprising: a gas extraction and sampling system configured to receive a drilling fluid sample from a flow of the drilling fluid at a surface of a borehole being drilled in a subterranean formation and extract a dissolved gas from the drilling fluid sample; a gas chromatograph to determine a concentration over time of at least one chemical species of the dissolved gas; a device configured to generate an area per concentration curve based on the concentration over time of the at least one chemical species, determine at least one concentration value of the at least one chemical species of the dissolved gas, and modify the at least one concentration value based on the area per concentration curve. For Embodiment 2, said device may be configured to modify the at least one concentration value by: fitting the area per concentration curve with a response curve; and applying the response curve to the determined concentration. For Embodiment 2, said device may be configured to modify the at least one concentration value by generating a corrected concentration of each species based on said applying the response curve to the determined concentration. For Embodiment 2, said gas extraction and sampling system may include a heat exchanger and a gas extractor configured to receive the drilling fluid sample from the heat exchanger, and wherein said extracting comprises circulating the drilling fluid sample through the heat exchanger and extracting gasses from the drilling fluid sample within the gas extractor. For Embodiment 2, said gas extraction and sampling system may be further configured to, during said extracting of the dissolved gas, circulate the drilling fluid sample between the extraction and sampling system and a containment vessel in response to a concentration of a species within the drilling fluid sample reaching a threshold. For Embodiment 2, said gas extraction and sampling system may be further configured to receive a drilling fluid sample from a flow of the drilling fluid at a surface of a borehole within a subterranean formation, wherein said receiving a drilling fluid sample comprises transporting the drilling fluid sample from downhole to the surface of the borehole during drilling operations. For Embodiment 2, said device may be configured to: determine a fluid formation characteristic of the subterranean formation using the at least one modified concentration value; and modify a hydrocarbon recovery operation based on the determined fluid formation characteristic.

Embodiment 3: A machine-readable medium having instructions stored thereon that are executable by a device to perform operations comprising: determining, using a gas chromatograph, a concentration over time of at least one chemical species of a dissolved gas extracted from a drilling fluid sample from a flow of drilling fluid received at a surface of a borehole being drilled in a subterranean formation; generating an area per concentration curve based on the concentration over time of the at least one chemical species; determining at least one concentration value of the at least one chemical species of the dissolved gas from the drilling fluid sample; and correcting bias caused by the gas extraction and sampling system, wherein correcting the bias comprises modifying the at least one concentration value based on the area per concentration curve. For Embodiment 3, said modifying the at least one concentration value may comprise: fitting the area per concentration curve with a response curve; and applying the response curve to the determined concentration. For Embodiment 3, said modifying the at least one concentration value may further comprise generating a corrected concentration of each species based on said applying the response curve to the determined concentration. For Embodiment 3, said fitting the area per concentration curve with a response curve may comprise generating the response curve based on the area per concentration curve. For Embodiment 3, the instructions may comprise instructions executable by the device to, during said extracting of the dissolved gas, circulate the drilling fluid sample between an extraction and sampling system and a containment vessel in response to a concentration of a species within the drilling fluid sample reaching a threshold. For Embodiment 3, the instructions may comprise instructions executable by the device to: determine a fluid formation characteristic of the subterranean formation using the at least one modified concentration value; and modify a hydrocarbon recovery operation based on the determined fluid formation characteristic.

What is claimed is:

1. A method comprising:
   extracting, using a gas extraction and sampling system, a dissolved gas from a drilling fluid sample;
   determining, using a gas chromatograph, a concentration over time of at least one chemical species of the dissolved gas;
   generating an area per concentration curve based on the concentration over time of the at least one chemical species, wherein the area per concentration curve is fitted with a response curve;
   determining at least one concentration value of the at least one chemical species of the dissolved gas from the drilling fluid sample; and
   correcting bias caused by the gas extraction and sampling system, wherein correcting the bias comprises modifying the at least one concentration value with the response curve to generate a corrected concentration value of each chemical species.

2. The method of claim 1, wherein the extraction and sampling system includes a heat exchanger and a gas extractor configured to receive the drilling fluid sample from the heat exchanger, and wherein said extracting comprises circulating the drilling fluid sample through the heat exchanger and extracting gasses from the drilling fluid sample within the gas extractor.

3. The method of claim 2, further comprising during said extracting of the dissolved gas, circulating the drilling fluid sample between the extraction and sampling system and a containment vessel in response to a concentration of a species within the drilling fluid sample reaching a threshold.

4. The method of claim 1, further comprising receiving a drilling fluid sample from a flow of the drilling fluid at a surface of a borehole within a subterranean formation, wherein said receiving a drilling fluid sample comprises transporting the drilling fluid sample from downhole to the surface of the borehole during drilling operations.

5. The method of claim 4, further comprising:
   determining a fluid formation characteristic of the subterranean formation using the at least one modified concentration value; and
   modifying a hydrocarbon recovery operation based on the determined fluid formation characteristic.

6. The method of claim 1, wherein the response curve is represented as an equation in which the corrected concentration value is defined as a function of the concentration value of the at least one chemical species.

7. The method of claim 6, wherein the equation that represents the response curve is at least one of a power log, a polynomial, and exponential.

8. A system comprising:
   a gas extraction and sampling system configured to,
     receive a drilling fluid sample from a flow of the drilling fluid at a surface of a borehole being drilled in a subterranean formation; and
     extract a dissolved gas from the drilling fluid sample;
   a gas chromatograph to determine a concentration over time of at least one chemical species of the dissolved gas;
   a device configured to,
     generate an area per concentration curve based on the concentration over time of the at least one chemical species, wherein the area per concentration curve is fitted with a response curve;
     determine at least one concentration value of the at least one chemical species of the dissolved gas; and correct bias caused by the gas extraction and sampling system, wherein correcting the bias comprises modifying the at least one concentration value with the response curve to generate a corrected concentration value of each chemical species.

9. The system of claim 8, wherein said gas extraction and sampling system includes a heat exchanger and a gas extractor configured to receive the drilling fluid sample from the heat exchanger, and wherein said extracting comprises circulating the drilling fluid sample through the heat exchanger and extracting gasses from the drilling fluid sample within the gas extractor.

10. The system of claim 9, wherein said gas extraction and sampling system is further configured to, during said extracting of the dissolved gas, circulate the drilling fluid sample between the extraction and sampling system and a containment vessel in response to a concentration of a species within the drilling fluid sample reaching a threshold.

11. The system of claim 8, wherein said gas extraction and sampling system is further configured to receive a drilling fluid sample from a flow of the drilling fluid at a surface of a borehole within a subterranean formation, wherein said receiving a drilling fluid sample comprises transporting the drilling fluid sample from downhole to the surface of the borehole during drilling operations.

12. The system of claim 8, wherein the device is configured to:
determine a fluid formation characteristic of the subterranean formation using the at least one modified concentration value; and
modify a hydrocarbon recovery operation based on the determined fluid formation characteristic.

13. The system of claim 8, wherein the response curve is represented as an equation in which the corrected concentration value is defined as a function of the concentration value of the at least one chemical species.

14. The system of claim 13, wherein the equation that represents the response curve is at least one of a power log, a polynomial, and exponential.

15. A machine-readable medium having instructions stored thereon that are executable by a device to perform operations comprising:
determining, using a gas chromatograph, a concentration over time of at least one chemical species of a dissolved gas extracted from a drilling fluid sample from a flow of drilling fluid received, by a gas extraction and sampling system, at a surface of a borehole being drilled in a subterranean formation;
generating an area per concentration curve based on the concentration over time of the at least one chemical species, wherein the area per concentration curve is fitted with a response curve;
determining at least one concentration value of the at least one chemical species of the dissolved gas from the drilling fluid sample; and
correcting bias caused by the gas extraction and sampling system, wherein correcting the bias comprises modifying the at least one concentration with the response curve to generate a corrected concentration value of each chemical species.

16. The machine-readable medium of claim 15, wherein said fitting the area per concentration curve with a response curve comprises generating the response curve based on the area per concentration curve.

17. The machine-readable medium of claim 15, wherein the instructions comprise instructions executable by the device to, during said extracting of the dissolved gas, circulate the drilling fluid sample between an extraction and sampling system and a containment vessel in response to a concentration of a species within the drilling fluid sample reaching a threshold.

18. The machine-readable medium of claim 15, wherein the instructions comprise instructions executable by the device to:
determine a fluid formation characteristic of the subterranean formation using the at least one modified concentration value; and
modify a hydrocarbon recovery operation based on the determined fluid formation characteristic.

19. The machine-readable medium of claim 15, wherein the response curve is represented as an equation in which the corrected concentration value is defined as a function of the concentration value of the at least one chemical species.

20. The machine-readable medium of claim 19, wherein the equation that represents the response curve is at least one of a power log, a polynomial, and exponential.

* * * * *